United States Patent [19]
Likuski et al.

[11] Patent Number: 4,919,595
[45] Date of Patent: Apr. 24, 1990

[54] FLUID DELIVERY SYSTEM WITH DEFICIT FLOW COMPENSATION

[75] Inventors: Robert K. Likuski, Castro Valley; Scott N. MacDonald, Pleasant Hill, both of Calif.

[73] Assignee: Beckman Instruments, Inc., Fullerton, Calif.

[21] Appl. No.: 21,389

[22] Filed: Mar. 3, 1987

[51] Int. Cl.$^5$ ............ F04B 49/00; B01D 15/08
[52] U.S. Cl. .................. 417/18; 417/22; 417/53; 210/198.2
[58] Field of Search .......... 417/18, 22, 53, 1; 210/101, 198.2

[56] References Cited

U.S. PATENT DOCUMENTS

| | | |
|---|---|---|
| Re. 31,608 | 6/1984 | Magnussen, Jr. . |
| 3,847,507 | 11/1974 | Sakiyama et al. ............ 417/22 |
| 4,045,343 | 8/1977 | Achener et al. . |
| 4,127,360 | 11/1978 | Carpenter ............ 417/5 |
| 4,137,011 | 1/1979 | Rock . |
| 4,255,088 | 3/1981 | Neuton ............ 417/1 |
| 4,311,586 | 1/1982 | Baldwin ............ 210/101 |
| 4,321,014 | 3/1982 | Eburn ............ 417/5 |
| 4,326,837 | 4/1982 | Gilson et al. . |
| 4,359,312 | 11/1982 | Funke et al. ............ 417/18 |
| 4,427,298 | 1/1984 | Fahy ............ 137/624.18 |
| 4,448,692 | 5/1984 | Nakamoto et al. ............ 417/18 |
| 4,492,524 | 1/1985 | Koch ............ 417/18 |
| 4,595,496 | 6/1986 | Carson ............ 210/198.2 |
| 4,705,459 | 11/1987 | Buisine ............ 417/53 |
| 4,714,545 | 12/1987 | Bente et al. ............ 417/5 |
| 4,808,092 | 2/1989 | Funke ............ 417/454 |

FOREIGN PATENT DOCUMENTS 48010 10/1980 Japan ............ 417/18

OTHER PUBLICATIONS

Catalog—Scientific Systems, Inc., Inside cover and pp. 1–15.

Primary Examiner—Leonard E. Smith
Assistant Examiner—David W. Scheuermann
Attorney, Agent, or Firm—William H. May; Paul R. Harder

[57] ABSTRACT

Method and apparatus for compensating for the deficiency in fluid flow occurring during the refill and piston chamber pump-up cycle of a single piston fluid pump are disclosed. The period of time during which the outlet valve is closed and no fluid is being delivered to the system is determined and the pump is driven at a speed greater than the normal delivery speed for a period of time such that the quantity of excess fluid delivered approximates the quantity of fluid that would have been delivered during the refill and pump-up period had the pump been delivering fluid at its normal delivery rate.

61 Claims, 4 Drawing Sheets

FLUID DELIVERY SYSTEM WITH DEFICIT FLOW COMPENSATION

This invention relates to fluid delivery systems and more particularly to a solvent delivery system useful in high performance liquid chromatography (HPLC).

The ideal HPLC pump would provide pulseless constant flow over a wide range of flow rates. Constant flow of the solvent insures reproducible retention times for a component in the sample at specific flow rates, column and mobile phase conditions. Pulseless flow eliminates undesirable effects sometimes attributed to pulsations, such as artifacts in the signal and disturbances of the column packing. A wide range of flow rates permits the use of a variety of analytical columns.

A number of HPLC pumps are commercially available. Through the use of interchangeable pump heads, flow rates from 0.001 ml/min. to 100 ml/min. are available at pressures as high as 10,000 psi. However, pumps with flow rate ranges from about 0.01 ml/min. to 10 ml/min. at pressures in the range of 500–6,000 psi are more typical.

Two fundamental styles of HPLC piston pumps are commercially available. The multi-piston HPLC pump, which commonly is a dual piston pump, is designed and constructed in such a way that one piston delivers solvent while the other piston is in its refill cycle. By coupling such pumps with pulse dampeners, fluctuations in pressure and flow are minimized. However, even these multi-piston pumping systems have non-uniform flow rates with significant pulsations.

With the advent of various control schemes, either mechanical (cam configuration) or electronic which provide rapid refill and pump-up, the performance of the single piston pump has equalled or exceeded multi-piston pumps. These pumps are inherently simpler, easier to maintain and the flow accuracy and reproducibility, particularly when coupled with pulse dampeners, equal or exceed that achievable utilizing dual piston pumps.

U.S. Pat. No. RE. 31,608 to H. T. Magnussen and assigned to the assignee of this invention illustrates a single piston pump and control circuitry which provides rapid refill and pump-up. In some of these prior art systems, system pressure is sampled prior to the flag signal (the beginning of refill) and the motor speed is increased during the refill cycle and is maintained until the pressure in the pump chamber reaches the previously stored system pressure. At this point the pump is returned to its normal pumping speed. Thus the rapid pump-up period ends when the piston chamber pressure reaches the stored system pressure.

In systems where two or more solvents are being supplied simultaneously through the use of two or more parallel connected pumps, this prior art compensation scheme results in cross talk between the systems inasmuch as one pump may control on system pressure sampled while the other pump is in its refill cycle. This problem is particularly severe where the percentage of one solvent is much higher than the other, for example 98% of one solvent to 2% of a second solvent.

The present invention provides a fluid or solvent delivery system which overcomes some of the disadvantages of the prior art, provides improved flow rate accuracy and reproducibility and automatically maintains the set flow rate even though one switches between solvents having different compressibility factors. Moreover, utilizing the control scheme of the present invention, cross talk in multiple pump systems is greatly reduced.

This invention is based upon accurately compensating for the deficit in flow in the system during the refill and piston chamber pump-up portions of the cycle. By accurately determining the length of time the outlet check valve is closed, i.e., the time during which no solvent flows out of the pump piston chamber, the quantity of undelivered fluid can be determined. After the outlet check valve opens, by driving the pump piston at a velocity above its normal delivery velocity an excess amount of fluid will be delivered to the system. By knowing the amount of excess fluid which will be delivered per unit of time at this higher rate, the duration of time necessary to compensate for the undelivered quantity of fluid can be computed. This period of time when the pump is delivering an excess amount of fluid to the system is termed herein "system pump-up" or the "system pump-up period". Many fixed and variable factors determine the time period during which the outlet check valve remains closed. The fixed factors include motor speed, cam profile, play in the piston drive mechanism and piston chamber compliance. The variable factors include gases dissolved in the solvent and solvent compressibility. By making the excess quantity of the fluid delivered during the system pump-up period equal to the deficit quantity, a high degree of compensation for all of these factors is achieved and accurate and reproducible fluid flow rates may be obtained without regard to these factors. Moreover the control scheme minimizes pressure fluctuations and greatly reduces cross talk between pumps in multi-pump systems.

As has been the case in the past the closing of the outlet check valve or the beginning of the refill cycle is determined by a flag driven along with the cam by the motor. The opening of the outlet check valve may be determined either directly as, for example, by detecting motion of the outlet check valve or solvent flow after the outlet check valve or indirectly such as by comparing system pressure with pump piston chamber pressure on a real time basis and inferring opening of the check valve when pump piston chamber pressure equals or exceeds system pressure, by detecting the change in slope of either piston chamber or system pressure, both of which occur upon opening of the check valve. In the preferred embodiment the opening of the check valve is inferentially or indirectly determined by utilizing a microprocessor to sample and hold the pressure and time at two different points during the piston chamber pump-up cycle, computing the slope of the pressure waveform and determining the time at which the pump pressure will reach a previously stored system pressure. By judiciously determining an appropriate percentage of the system pressure and utilizing that factor, over or undercompensation of the deficit flow may be achieved.

Other features and advantages of this invention will become apparent to those skilled in the art from the following detailed description of applicant's invention when taken in conjunction with the accompanying drawings.

Figure 1:
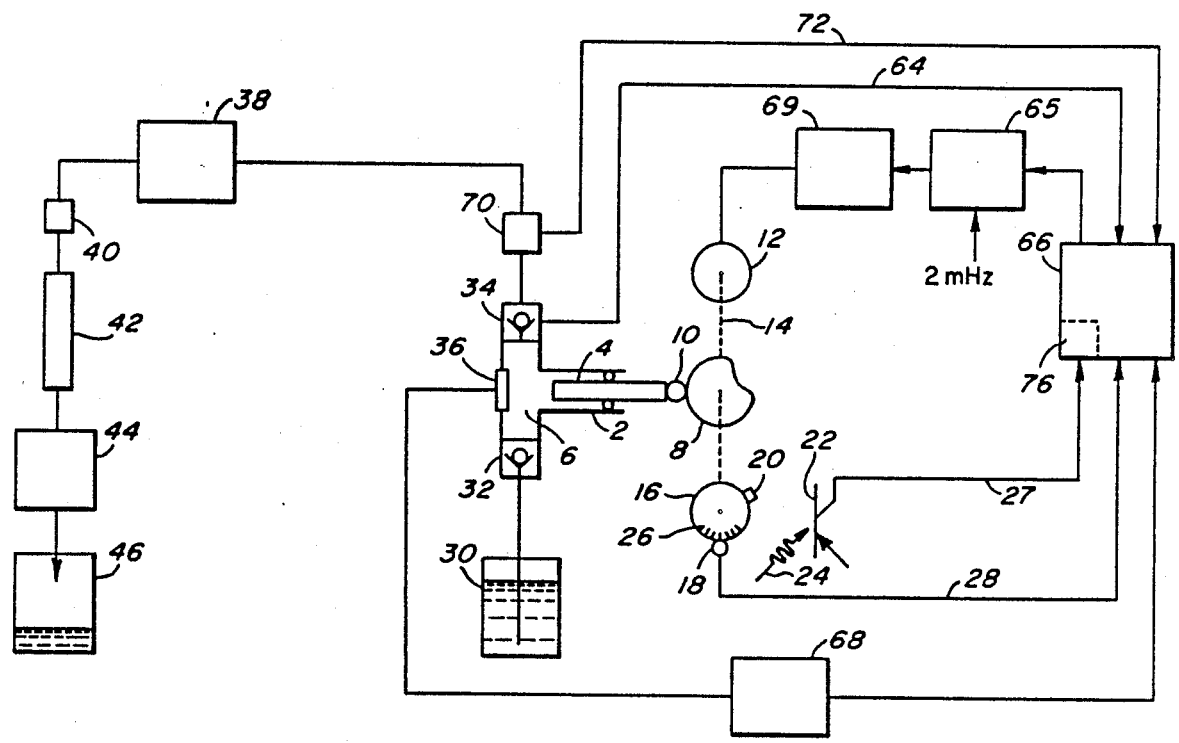
FIG. 1 is a schematic illustration of a high performance liquid chromatography system including a fluid or solvent delivery system constructed in accordance with the teachings of this invention.

Referring now to FIG. 1 there is schematically illustrated a solvent delivery system constructed in accordance with the teachings of this invention and which is suitable for use in high performance liquid chromatography. The system comprises a reciprocating single piston pump 2 having a piston 4 reciprocating in pumping chamber 6. The piston is reciprocated by a suitably shaped cam 8 through a coupling 10 in any manner well known in the art. The cam 8 is driven by a motor 12 through shaft 14 the speed of the motor being regulated through a suitable motor control circuit which will be described in more detail hereafter. Also coupled to shaft 14 may be a suitably encoded disc 16 which with sensor 18 provides data to the motor control circuit to indicate or allow to be determined the precise angular position of the cam. Disc 16 may also contain a flag 20 which with a photo sensitive diode 22 and a light source 24 is utilized to indicate a reference or reset point, usually top dead center or the start of the refill cycle as will be explained more fully hereinafter. It is understood that the light source and diode are positioned on opposite sides of the disc such that the flag interrupts the light to provide a pulse on line 27 at the reference or reset point which pulse provides an input to the motor control circuit or a microprocessor. It is obvious that the flag could be a notch in the disc to allow passage of light at the reference point rather than an interruption of light. Sensor 18 may be a light source and diode positioned on opposite sides of the encoder disc 16 which may contain a series of slots 26 around its periphery (only some of which are shown) such that a series of pulses are provided on line 28 as the motor moves. By counting the number of pulses after the flag or reset pulse, the precise angular position of the motor and cam, and the linear position of the piston, may be determined. If the motor is of the stepper motor type, the angular position of the motor and cam can be determined by counting the pulses to the stepper motor. In this case the encoder disc is not necessary but the flag is retained for periodic reference and check. The following discussion presumes the use of a stepper motor.

Interposed between pump 2 and the solvent reservoir 30 is an inlet check valve 32 which opens on the suction or refill stroke of piston 4, allowing solvent to be drawn into the pumping chamber 6 during the refill cycle. An outlet check valve 34 is interposed between the pumping chamber 6 and the remainder of the system and allows the solvent to be delivered to the system during the pumping stroke of piston 4. Check valves 32 and 34 may be constructed as an integral part of the pump and pump chamber 6 or closely coupled thereto. As is well known in the art and as will be explained in more detail hereafter during the pumping stroke outlet check valve 34 is open and inlet check valve 32 is closed. At the end of the delivery stroke outlet check valve 34 closes and after decompression of the pumping chamber on the return stroke, inlet check valve 32 opens to admit solvent into the pumping chamber. As piston 4 commences its compression stroke, inlet check valve 32 closes, thereby preventing return of the solvent to reservoir 30 and, after recompression of the pumping chamber to the system pressure, outlet check valve 34 opens and allows delivery of the solvent to the remainder of the chromatographic system. Pump 2 has a pressure sensor 36 built into the pumping chamber to sense the pressure within pumping chamber 6. When outlet check valve 34 is open, piston chamber pressure equals or exceeds system pressure. Piston chamber pressure may exceed system pressure because of a flow induced pressure drop across the outlet check valve and associated system tubing.

The solvent delivery system is connected into a liquid chromatographic system through suitable tubing connected from the outlet check valve 34 through a pulse damper 38 (which may be an integral part of the pump), an injection valve 40, a chromatographic column 42, a detector 44 and then to a waste or collection vessel 46.

As is well known to those skilled in the art a solvent mixing system may be substituted for solvent reservoir 30 if it is desired to utilize and mix a plurality of solvents prior to pressurization. A fraction collector or other appropriate collection means may be substituted for the collection vessel 46. Further, in some forms of chromatography two or more pumps may be connected in parallel to allow two or more solvents to flow in any desired proportion through the column simultaneously. In gradient chromatography these proportions are time programmed thus requiring the pump delivery flow rates to be varied during the run.

Figure 2:
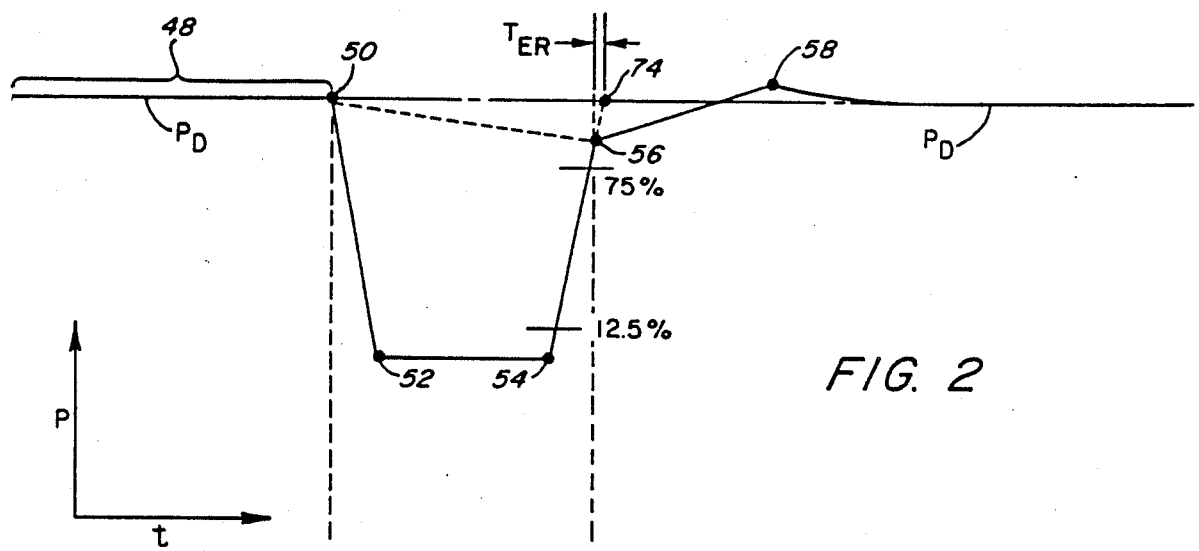
FIG. 2 is a pressure versus time waveform showing both pump piston chamber pressure and system pressure.
Figure 3:
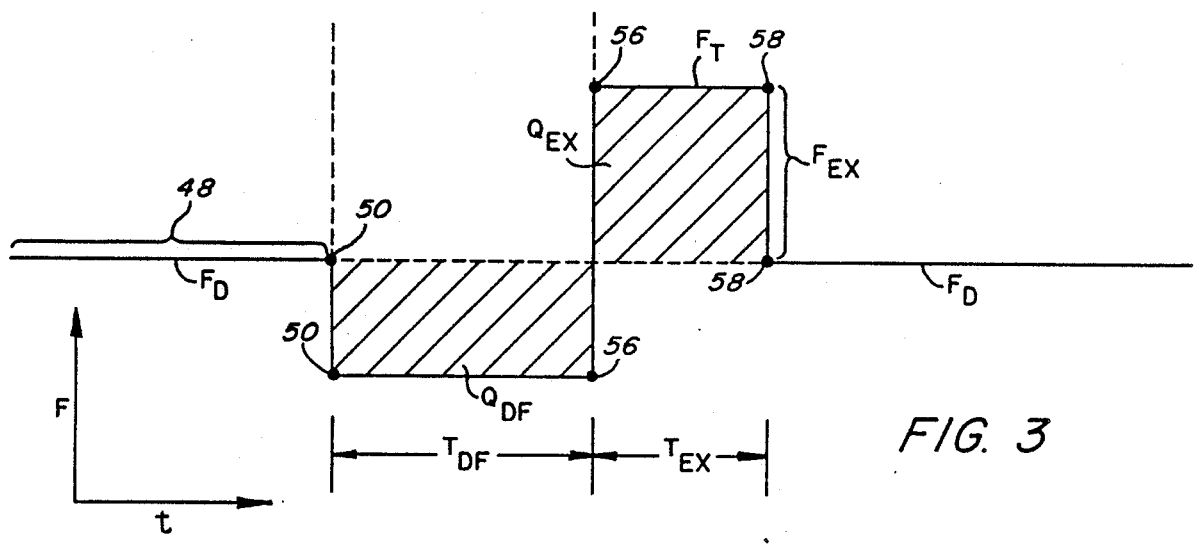
FIG. 3 is a flow rate versus time waveform of the flow at the outlet of the pump piston chamber.

Referring now to FIGS. 2 and 3 there is shown, in idealized and somewhat exaggerated form, time graphs of pressure and flow rate for a solvent delivery system incorporating the concepts of this invention. FIG. 2 is a combination pump chamber pressure and system pressure waveform versus time while FIG. 3 illustrates solvent flow rate out of the pump chamber and into of the remainder of the chromatographic system. Common portions of the pumping cycle in both FIGS. 2 and 3 are designated by like numerals.

The graphs commence with piston 4 traveling at a constant linear rate in the piston chamber in the delivery direction and with the outlet check valve open and the inlet check valve closed. That portion of the cycle (sometimes referred to as "normal delivery") is illustrated by the lines 48 and the piston chamber pressure and the system pressure are substantially equal and at the desired delivery pressure $P_D$. System flow rate is at the desired delivery flow rate $F_D$.

At point 50, piston 4 reaches the extent of its travel and begins to retract, decreasing the pressure within the piston chamber resulting in the outlet check valve closing and the flow rate out of the piston chamber (FIG. 3) drops to zero. At point 50 both the outlet and the inlet check valves are closed since the pressure within the piston chamber is below system pressure and above atmospheric and the pump chamber pressure rapidly decreases as the piston retracts until the pressure therein referenced to atmospheric is zero or slightly negative as illustrated at point 52 in FIG. 2 at which time the inlet check valve opens. Thus, the solid line between points 50 and 52 represents pump piston chamber pressure only, since the outlet check valve is closed. This decrease in pressure from system pressure to zero or slightly below allows for decompression of the fluid and relaxation of the pump seals, chamber walls, etc., commonly termed piston chamber compliance.

At point 52, the inlet check opens and remains open as the pump piston continues its withdrawal or refill stroke drawing into the chamber solvent from the solvent reservoir. As the pump piston reverses its direction and begins to compress the fluid the pressure starts to rise and the inlet check valve closes at point 54. For a short period of time the increase in pressure may be small as any undissolved gases are driven back into solution but as the pump piston continues its compression stroke the pressure within the pump chamber starts to rise rapidly. The time required to drive gases back into solution is small and is not illustrated in FIG. 2. While the chamber pressure is below system pressure, the outlet check valve remains closed. During this period, herein called piston chamber pump-up, the pressure within the pump chamber is increased, compressing the solvent fluid and seals, expanding the piston chamber (piston chamber compliance) and continues to build until the chamber pressure equals or exceeds system pressure and the outlet check valve opens at point 56. As is obvious, for a given pump operating at the same speed, the slope of line 54-56 will be dependent upon the compressibility of the solvent, the more compressible the fluid the more shallow the slope. Because of the compliance of the pulse damper 38, the resistance of column 42 and the other resistance and compliance factors of the system, when the outlet check valve closes at point 50 the system pressure does not follow pump piston chamber pressure but begins to slowly decay until pump chamber pressure and system pressure are again equal and the outlet check valve opens at point 56. Thus system pressure during the period when the outlet check valve is closed is represented by the dashed line between points 50 and 56. Also in FIG. 3, since the outlet check valve is close between points 50 and 56, the flow out of the piston chamber is zero.

As is also well known by those skilled in the art, it is common practice to increase motor drive speed to provide rapid refill and rapid piston chamber pump-up in an effort to minimize the time period when no fluid is being delivered to the system and thereby minimize pulsations therein. As previously noted, U.S. Pat. No. Re. 31,608 to Magnussen teaches one such system. If the linear speed of the piston used during the piston chamber pump-up portion of the pumping stroke is maintained at a high value after the outlet check valve opens, the flow into the system will be greater than the flow $F_D$ during the normal delivery cycle and will continue at this excess rate until the motor speed or pump piston speed is returned to its normal delivery rate. The point at which the piston velocity returns to its normal delivery rate is indicated at point 58. Referring now to FIG. 3, the total flow rate illustrated by the line $F_T$, which occurs while the pump piston is traveling at a rapid system pump-up velocity and occurs between the time the outlet check valve opens at 56 and the time when the piston velocity is returned to the normal delivery velocity at 58, is equal to the sum of the delivery flow rate $F_D$ plus an excess flow represented by $F_{EX}$. This excess flow $F_{EX}$ and time period $T_{EX}$ has been termed herein "system pump-up" and the "system pump-up time period" to distinguish from piston chamber pump-up which occurs before the outlet check valve opens. Referring again to FIG. 2, while the pump is still in its rapid pump-up mode and after the outlet check valve opens at point 56, pump chamber pressure and system pressure continues to rise until the point 58 at which time the pump is returned to its normal delivery rate. Generally this pressure will slightly exceed normal delivery pressure and when the pump returns to normal delivery speed, the system pressure (and pump chamber pressure) asymptotically decays until it again reaches normal system delivery pressure $P_D$.

As has been previously discussed it is advantageous to automatically compensate a solvent delivery system for the deficiencies in flow which result when a single piston rapid refill and rapid piston chamber pump-up pump executes the refill and chamber pump-up portion of the cycle.

Referring again to FIG. 3 the quantity of fluid which is not delivered during refill and piston chamber pump-up is represented by the shaded area $Q_{DF}$ and is defined as $$Q_{DF} = F_D \cdot T_{DF} \qquad (1)$$

where $F_D$ is the flow rate which occurs during the normal delivery portion of the cycle and $T_{DF}$ is the time period between points 50 and 56 when the outlet check valve is closed.

Similarly the excess quantity of fluid that is delivered during the time period $T_{EX}$ when the pump piston is traveling at a higher velocity than its normal delivery speed, i.e., from point 56 to point 58, is represented by the shaded area QEX If the pump piston velocity, and therefore $F_{EX}$, is constant during the period $T_{EX}$, the excess quantity is then defined as $$Q_{EX} = F_{EX} \cdot T_{EX} \qquad (2)$$

In the case where the piston velocity, and therefore the flow rate $F_{EX}$, is not constant, the right hand side of equation (2) is replaced by an integral of $F_{EX}$. Thus, $$Q_{EX} = \int_0^{T_{EX}} F_{EX} \, dt \qquad (3)$$

From an inspection of FIG. 3 it is apparent that if there is to be no deficiency or excess in the flow resulting from the refill and piston chamber pump-up portion of the cycle, the following equation must be satisfied:

$$Q_{EX} = Q_{DF} \qquad (4)$$

Substituting equations (1) and (2) into equation (4) we have $$F_{EX} \cdot T_{EX} = F_D \cdot T_{DF} \qquad (5)$$

Solving equation (5) for $T_{EX}$ we have $$T_{EX} = \frac{F_D}{F_{EX}} \cdot T_{DF} \qquad (6)$$

In the case where pump and piston speed is maintained constant during the period $T_{EX}$ such that the flow rate is a constant, it is apparent that the ratio of the delivery flow rate $F_D$ to the excess flow rate $F_{EX}$ itself reduces to a constant. Therefore the time $T_{EX}$ during which the pump motor speed must be maintained at the high level to deliver the excess quantity is equal to the time $T_{DF}$ when the outlet check valve is closed multiplied by a constant.

The initiation of time period $T_{DF}$ is readily determined. $T_{DF}$ starts when the pump piston reaches the end of its compression stroke and starts to return in the opposite direction commencing its refill stroke. This point is determined by the shape of the drive cam and therefore the angular position of the drive motor and may be readily determined by a flag associated with the cam drive shaft interrupting or activating a photon detector as previously described and as more specifically disclosed in Magnussen, U.S. Pat. No. Re. 31,608. This signal can also be used to trigger an increase in motor speed. The end of the time period $T_{DF}$ coincides with opening of the outlet check valve. This point in time and thus the duration of time period $T_{DF}$ may be measured directly or it can be indirectly determined or deduced.

Figure 4:
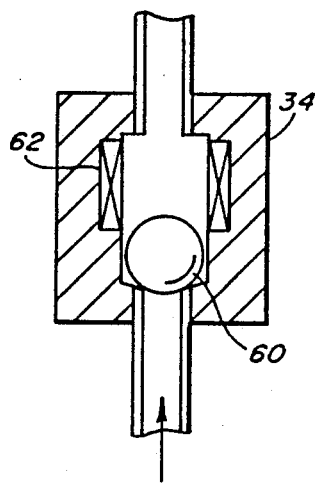
FIG. 4 is an outlet check valve, partially in cross section, suitable for use in this invention.

Referring now to FIG. 4 an outlet check valve 34 is illustrated partially in cross section. As is shown in FIG. 4 the check valve ball 60, when the valve is in the closed position, is seated against the inlet preventing return of fluid from the system back into the pump chamber. When the pump chamber pressure rises above system pressure the ball is raised from the seat allowing flow through the check valve in the direction of the arrow. In practice the ball is carried by the flowing fluid to a stop on the outlet side of the check valve. Suitable channels, not illustrated, in that stop prevent the ball from blocking passage of the fluid at the outlet. If ball 60 is made of a magnetized material and the check valve is provided with a winding or coil of wire 62, movement of the ball will induce a voltage in coil 62 which may be detected. More suitably, motion of a metal but not necessarily magnetized check valve ball may be detected by connecting the coil 62 into a resonant circuit, motion of the ball changing the inductance of the coil and thereby shifting the resonant frequency. A shift in the resonant frequency may be readily detected and utilized to indicate movement of ball 60 and the opening of the check valve. As shown in FIG. 1, the signal from the coil or other motion detector for the outlet check valve may be transmitted over line 64 to suitable computing circuitry 66 in the motor control circuit. In the preferred embodiment the computing portion 66 of the motor control circuitry is a microprocessor. Alternatively, a photo diode transmitter-detector pair could be substituted for coil 62 and the opening of check valve 34 optically detected. The closing of the outlet check valve may also be sensed by these methods and therefore the flag signal omitted. However, since check valve closing always occurs at very nearly the same point in the cycle, i.e., top dead center or the beginning of refill, its closing can accurately be indicated through the use of the flag signal. However, because of operating pressure and solvent compressibility differences, the same is not true for check valve opening and the use of a flag to indicate check valve opening is not sufficiently accurate at high pressures although such a flag signal (or the count for a stepper motor) could be used to approximate the opening of the outlet check valve at low pressures.

The opening of outlet check valve 34 may also be determined indirectly. Referring again to FIG. 2 it should be noted that the slope of the pressure waveform changes markedly at point 56 when the outlet check valve opens. This change in slope of the waveform occurs, even though pump piston speed is constant, because the piston initially is repressurizing only the piston chamber volume when the check valve is closed but after it opens, it is repressurizing the entire chromatographic system volume. Referring again to FIG. 1, piston chamber pressure transducer 36 is connected through analog to digital converter 68 to the computing part of the motor control circuit 66. By closely monitoring piston chamber pressure and detecting the change in slope at 56 the opening of the check valve can be determined. Alternatively, by placing a pressure transducer or sensor 70 (see FIG. 1) in the line after the outlet check valve 34, system pressure may be monitored. As illustrated in FIG. 2, system pressure, indicated by the dashed line between points 50 and 56, slowly decays during the period of time when the outlet check valve is closed. When the outlet check valve initially closes at 50, the piston chamber pressure drops rapidly to near zero or slightly negative during the refill portion of the cycle. As the pump begins its pump-up stroke at 54 the pressure in the pump chamber rises rapidly and by comparing system pressure with pump chamber pressure during this pump-up period the time when outlet check valve 34 opens may be deduced from the point where piston chamber pressure becomes equal to or exceeds system pressure. It should be noted that system pressure also changes slope at point 56 when the outlet check valve opens. Moreover, this slope changes from negative to positive. By monitoring only system pressure and detecting this change in slope, the outlet check valve opening may be determined. In fact it may be easier to detect the check valve opening using system pressure if the change in the slope of the pump chamber pressure curve is slight or is obscured by "ringing" which normally accompanies the opening of the outlet check valve (see FIG. 6 and the accompanying text).

Other methods of indirectly detecting outlet check valve opening may be utilized. For example, instead of utilizing pressure transducer 70, a thermistor of very low thermal mass may be substituted and placed in the fluid stream on the outlet side of the check valve. The thermistor increases in temperature when the outlet check valve is closed because the fluid surrounding the thermistor is stationary. When the outlet check valve opens, solvent begins to move past the thermistor carrying away heat and the temperature of the thermistor decreases. This decrease in temperature can be readily detected by an appropriate electronic circuit. Alternatively, detector 70 may comprise a "paddle wheel" or turbine which is driven by motion of the solvent, rotation of the wheel (or lack thereof) being suitably detected and transmitted to the computing part of the control circuit 66. Still further, a thin strain gauge or vane may be inserted into the fluid stream which is bent by the flow of solvent thereby changing its resistance, which change in resistance may be detected to determine the opening of outlet check valve 34. Regardless of the type of detector 70 utilized, the output signal therefrom may be transmitted over line 72 to the computing part of the motor control circuit 66.

In the preferred embodiment the computing part 66 of the motor control circuit is a microprocessor, the motor speed control output thereof being applied to a step generator 65 which also has a 2 megahertz clock signal applied thereto, the output of the step generator being connected to a stepper motor drive circuit 69 which provides micro step pulses to the stepper motor at a rate determined by the microprocessor. In the preferred embodiment, the slope of the chamber pressure pump-up waveform 54-56 is determined and the point in time when this line would reach system pressure is taken as the point in time when the outlet check valve opens. Such procedure results in slight overcompensation of the flow deficit which is intended for reasons which will be hereinafter explained. However, either overcompensation or undercompensation is possible by judicious selection of an appropriate percentage of the system pressure and using this to indicate check valve opening as will be more fully explained hereafter.

At some point in time along line 48 of FIG. 2 when the pump is at its normal delivery speed and normal delivery conditions apply and usually shortly before the outlet check valve closes at 50, system pressure is sensed and stored by the microprocessor sampling pump chamber pressure through transducer 36 or transducer 70. As previously indicated, when the pump piston reaches the end of the pumping stroke and starts its refill cycle flag 20 interrupts the light to (or allowed light to fall on) photo detector 22 and provides a reset or reference pulse on line 27 to microprocessor 66. This reset or reference pulse is utilized to start a timer or counter 76 which may be internal to the microprocessor 66. This action starts the beginning of the time period $T_{DF}$. Further, by counting the number of pulses to the stepper motor 12 after this flag or reset pulse, the precise position of cam 8 may be determined. At a point in time during the refill cycle just before point 54 the microprocessor 66 commences to sample pump piston chamber pressure and continues to sample chamber pressure once every 1 millisecond thereafter. By utilizing the time at which the chamber pressure reaches two predetermined points on the curve selected prior to the opening of the outlet check valve, say when the chamber pressure reaches 12.5% and 75% of the stored system pressure, the slope of line 54-56 may be determined and the time when pump piston chamber pressure would reach any other pressure if the outlet check valve remained closed can be calculated. Thus, since the time at which deficit flow commenced at 50 is known from the flag signal and the end of the period can be predicted from the slope of line 54-56, the time $T_{DF}$ may be determined. That time can then be substituted into equation (6) and the time period that the excess flow should continue may be calculated.

The pressure to which the piston chamber pressure is extrapolated may be selected in several ways. Most simply, it may be a percentage of the pressure measured and stored prior to the closing of the outlet check valve. It could also be determined by calculating the pressure at which the straight line approximation of the system pressure and the piston chamber pressure would intersect. In single pump systems the system pressure can be assumed to decay exponentially to zero pressure when the outlet check valve is closed. A system time constant can be determined from the system resistance and compliance and used in the formula for exponential decay to approximate the system pressure at a time approximating the opening of the outlet check valve.

As stated, the preferred embodiment actually utilizes a time when an extension of line 54-56 would be equal to the sampled delivery system pressure, i.e., point 74 in FIG. 2, as the end of the time period $T_{DF}$ or the opening of the outlet check valve 34. Thus, the time $T_{DF}$ is actually slightly longer by the time period $T_{ER}$ which represents the time period between the time when the outlet check valve actually opens and the time when $T_{DF}$ is assumed to terminate. This time period is very small and provides an overcalculation or indication of the flow deficiency $Q_{DF}$ and therefore a slight overcompensation for the reasons set forth hereinafter.

Figure 5:
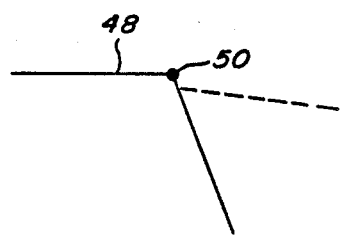
FIG. 5 is an enlarged view of the pressure versus time waveform in the area where the outlet check valve closes.

As has been previously indicated the waveforms of FIGS. 2 and 3 are in somewhat idealized form. Referring to FIG. 5, the area of the pressure curve in the vicinity of point 50 or the point at which piston ends its delivery stroke is shown in greater detail. As shown, the system pressure actually follows piston chamber pressure for a very short period of time and then starts to slowly decrease, the slope thereof being primarily dependent upon column resistance and the compliance of the pulse dampener. The reason for this is that as the piston commences its refill stroke a small amount of fluid from the system flows back into the piston chamber prior to actual closing of the check valve. Thus, $Q_{DF}$ is slightly greater than the quantity calculated utilizing the idealized form of FIG. 3 and equation 6 and thus, to make up for this deficiency, the preferred embodiment utilizes the point in time where the line 54-56 would intersect the original system pressure so that $T_{DF}$ is slightly longer than actual. It should be recognized that by judicious selection of the parameters which are used to determine the end of the time period $T_{DF}$, which approximate the opening of the outlet check valve, over or undercompensation may be obtained. For example if the system pressure drop-out during refill is small and, one utilizes the point at which chamber pressure reaches 90% of stored system pressure as the time of outlet check valve opening undercompensation will occur while by selection of the 110% point, overcompensation will occur. By appropriately selecting a percentage of the stored system pressure as the point of opening of the outlet check valve, over or undercompensation and the amount thereof may be obtained. It should also be noted that the upper point on line 54-56 used to determine the pressure waveform slope, in the preferred embodiment 75%, must be selected to insure that the outlet check valve has not yet opened.

Figure 6:
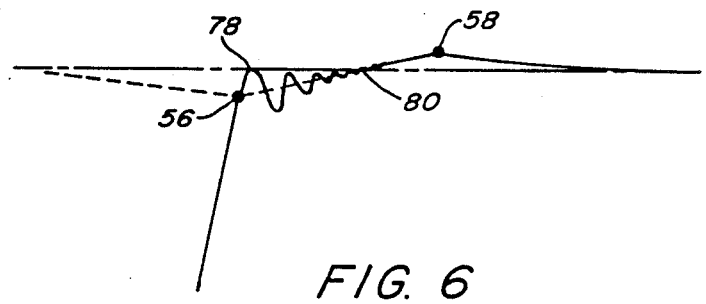
FIG. 6 is an enlarged view of the pressure versus time waveform in the area where the outlet check valve opens.

A more detailed analysis of the principles taught herein show that in a fully compensated pump, the pressure at the end of system pump-up exceeds the system pressure measured just prior to closing of the outlet check valve. (See 58, FIG. 2 and 6). Also, the more the system pressure drop-out during refill, the more the overshoot. The prior art algorithm undercompensates and a serious problem therewith is illustrated in FIG. 6. Referring now to FIG. 6 the area of the pressure curve of FIG. 2 in the vicinity of point 56, the opening of the outlet check valve, is shown in greater detail. Measurement of the pressure waveform near outlet check valve opening shows that opening is accompanied by ringing as indicated at 78 in FIG. 6. Also as previously indicated, certain of the prior art teach termination of the pump-up period when pump chamber pressure reaches the system pressure measured prior to the closing of the outlet check valve. The ringing shown in FIG. 6 causes termination of the pump-up period at 78 when the pressure wave first reaches the stored system pressure rather than at point 80 which is where the chamber pressure would have reached system pressure in the absence of ringing. This causes a premature termination of the pump-up cycle. The ringing, however, may provide yet another means of determining when the outlet check valve opens.

Figure 7:
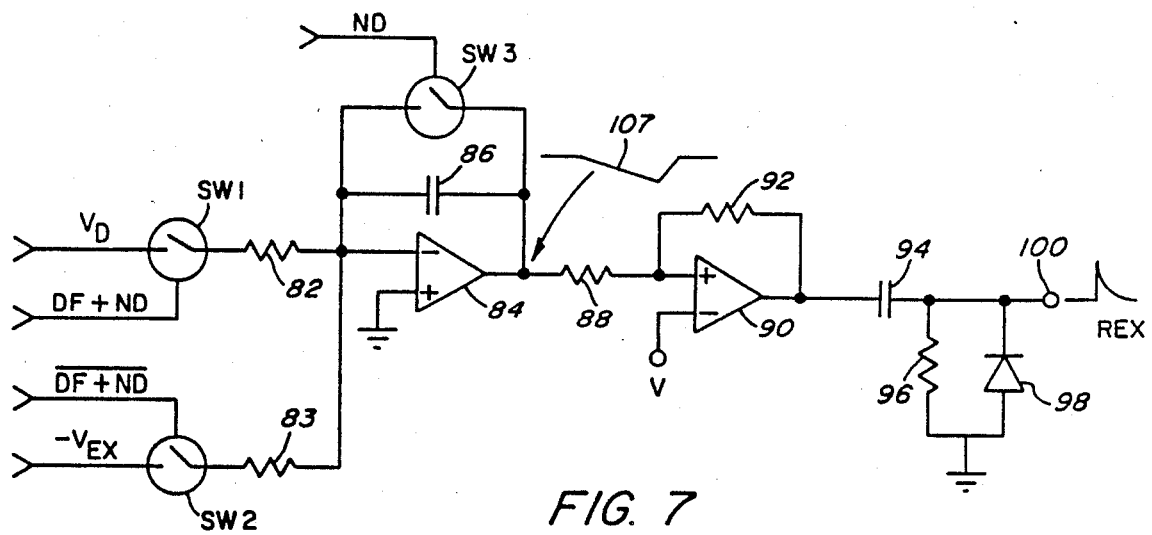
FIG. 7 is an analog circuit suitable for generating a signal indicative of the time when the excess flow period ends.
Figure 8:
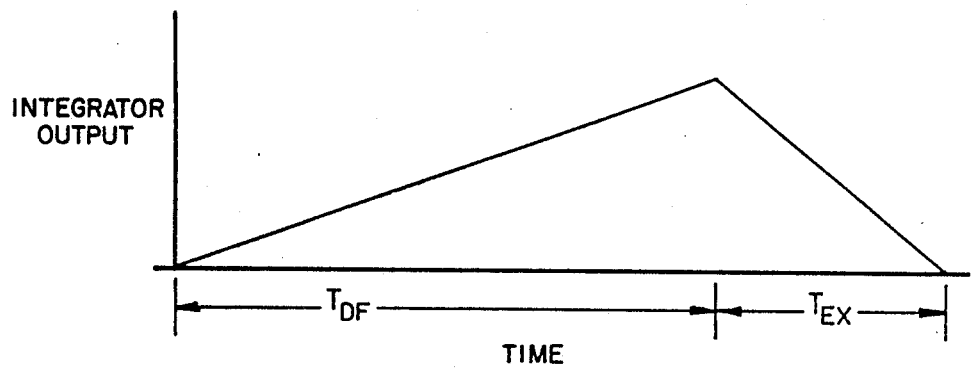
FIG. 8 is a waveform showing the output of the integrator of FIG. 7 as a function of time.
Figure 9:
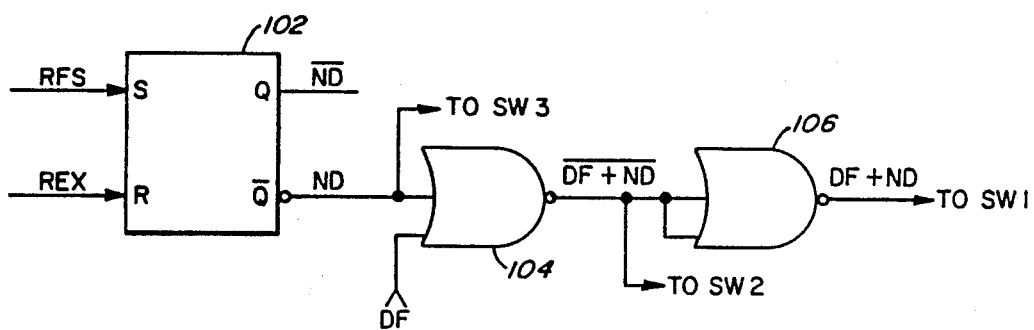
FIG. 9 illustrates a logic diagram to provide certain of the control signals needed in the circuit of FIG. 7.

An alternate embodiment utilizing an analog circuit rather than a microprocessor to calculate $T_{EX}$ from $T_{DF}$ in real time is illustrated in FIGS. 7–9. It is a fundamental theory of this invention to drive the pump at a high rate for a time period after the outlet check valve opens to create an excess flow in the system equal to the deficiency in the flow while the pump was in the refill and piston chamber pump-up portion of the cycle and thus satisfy equation 4.

We know also that $$Q_{EX} = \int_0^{T_{EX}} F_{EX} \, dt \quad (7)$$

and $$Q_{DF} = \int_0^{T_{DF}} F_D \, dt \quad (8)$$

If $T_{DF}$ is known, $T_{EX}$ can be readily determined in this general case by integrating a voltage $V_D$ proportional to $F_D$ for a time $T_{DF}$ and then integrating a voltage $-V_{EX}$ proportional to $-F_{EX}$ until the integrator reaches its starting value, typically zero volts. These voltages are typically available in analog circuits in which a servo motor is used to drive the pump. During normal delivery a voltage $V_D$ is applied to the servo and at other times the voltage $V_D + V_{EX}$ is applied. $T_{EX}$ would be equal to the time required for the integrator to reach its starting value after the integrated voltage was switched from $V_D$ to $-V_{EX}$. FIG. 8 illustrates this integration for the special case where $F_{EX}$ is constant, i.e., that the motor is being driven at a constant rate during the excess flow time period.

Referring now to FIG. 7, the voltage $V_D$ is connected through switch SW1 and resistor 82 to the inverting terminal of an integrator which comprises an operational amplifier 84 and capacitor 86 connected between the output and the inverting terminal, switch SW3 being connected across capacitor 86. The other terminal of the integrator is connected to circuit ground. Also connected to the inverting terminal of the integrator through switch SW2 and resistor 83 is the voltage $-V_{EX}$. Resistor 83 will have the same valve as resistor 82. The output of the integrator is connected through resistor 88 to the positive input of a comparator 90 having a fixed voltage V connected to its negative input terminal. A feedback resistor 92 is connected between the output and the positive input terminal of comparator 90. Connected to the output of comparator 90 is a series connected capacitor 94 and parallel connected resistor 96 and diode 98 for pulse shaping. The output terminal 100 of the circuit is connected to the reset terminal of the bistable flip-flop 102 of FIG. 9. Resistor 82 or resistor 83 and capacitor 86 determine the integrator time constant and resistors 88 and 92 provide hysteresis for the comparator. In FIG. 7 subscripts are used which have been used heretofore to specify time intervals. High true logic levels are shown without a bar above the symbol and low true logic levels are designated with a bar above the symbol. The switches shown in FIG. 7 are high true, where true corresponds to closure. The "+" symbol designates the logic "OR"

function. The voltage V is either ground or a voltage source that can be varied on either side of ground.

The logic symbols utilized are defined as follows:
DF is a logic level corresponding to the deficit flow time period $T_{DF}$;
ND is a logic level corresponding to the time interval when the motor is at its normal delivery speed;
REX is a logic pulse corresponding to the end of the excess flow time period;
RFS is a logic pulse corresponding to the start of the refill time interval or the flag signal in FIG. 1. This symbol is not used in FIG. 7 but is utilized in FIG. 9.

In operation switch SW1 is closed during the interval of deficit flow (DF is high) or during the normal delivery portion of the cycle (ND is high). Thus SW1 is open only during system pump-up i.e. only during the excess flow period. Switch SW3 however is also closed during the normal delivery portion of the cycle and renders the integrator inoperative during this period Thus, during the period $T_{DF}$ when the outlet check valve is closed and no flow is occurring in the system a voltage $V_D$ proportional to the deficit flow is being applied to the integrator and a negative going ramp (shown positive in FIG. 8) is generated at the integrator output as indicated by waveform 107. Thus, the integrator is ramped down at a rate proportional to the voltage $V_D$ during the time of deficit flow or when the outlet check valve is closed.

The logic level $\overline{DF+ND}$ is applied to switch SW2. Thus, SW2 is closed when SW1 is open and vice versa and SW2 is closed only when the system is in the excess flow period. During this period, ND is low, SW3 is open and the integrator is operative. During this period, voltage $-V_{EX}$ proportional to the excess flow rate is applied through switch SW2 to the integrator and the integrator ramps up as shown by waveform 107 (down in FIG. 8). When the integrator output returns to zero volts (or the voltage set by voltage V) the comparator provides an output pulse REX which indicates the end of the rapid system pump-up cycle.

Referring now to FIG. 9, support logic for the integrator circuit of FIG. 7 is illustrated. A bistable flip-flop 102 has applied to its set terminal the start of refill or flag signal RFS and to its reset terminal the output REX of the circuit of FIG. 7 i.e., a pulse indicating the end of the system pump-up period. As is well known when the flip-flop is in reset Q is low and $\overline{Q}$ is high. When the flip-flop is in set, Q is high and $\overline{Q}$ is low. By applying the flag or start refill signal RFS to the set terminal and the end of the excess flow or system pump-up signal REX to the reset terminal, Q is high only when the motor is at its normal delivery speed (ND). ND is applied directly to switch SW3 in FIG. 7 and to one terminal of NOR gate 104. The logic level ND can also be utilized by the external circuitry to switch the pump between its normal delivery speed corresponding to $V_D$ and its rapid speed corresponding to $V_D + V_{EX}$. The signal DF indicating that the outlet check valve is closed and that deficit flow is occurring is applied to the other terminal. The logic level DF may be generated through the use of another bistable flip-flop applying RSF to the set terminal and a pulse coinciding with the opening of the outlet check valve to the reset terminal. The pulse coinciding with the opening of the outlet check valve can be generated through the use of any of the methods previously described. The output of gate 104, $\overline{DF+ND}$, is applied to switch SW2 and to both inputs of a second NOR gate 106. The output of NOR gate 106, DF +ND is applied to switch SW1.

In FIG. 3 it has been assumed that the pump motor speed during the refill and rapid piston chamber pump-up period and the system pump-up period are the same. Thus, for any given delivery rate the motor has a first constant linear speed during the normal delivery period and a rapid but constant speed during the refill and chamber pump-up and system pump-up periods. It is obvious, of course, that the pump speed during the rapid refill, chamber pump-up and system-pump-up periods need not be the same nor do they need to be constant. In many stepper motors, torque decreases as angular velocity increases. Thus, in some instances where system pressure is high, it may be desirable to ramp the motor speed downward as the pressure builds. It is merely necessary to integrate the area under the excess flow curve to determine the appropriate time period $T_{EX}$. Further, it should be apparent that rapid refill is not an essential element of this invention although, from a practical standpoint, it is desirable to reduce the refill time period as much as possible.

Figure 10:
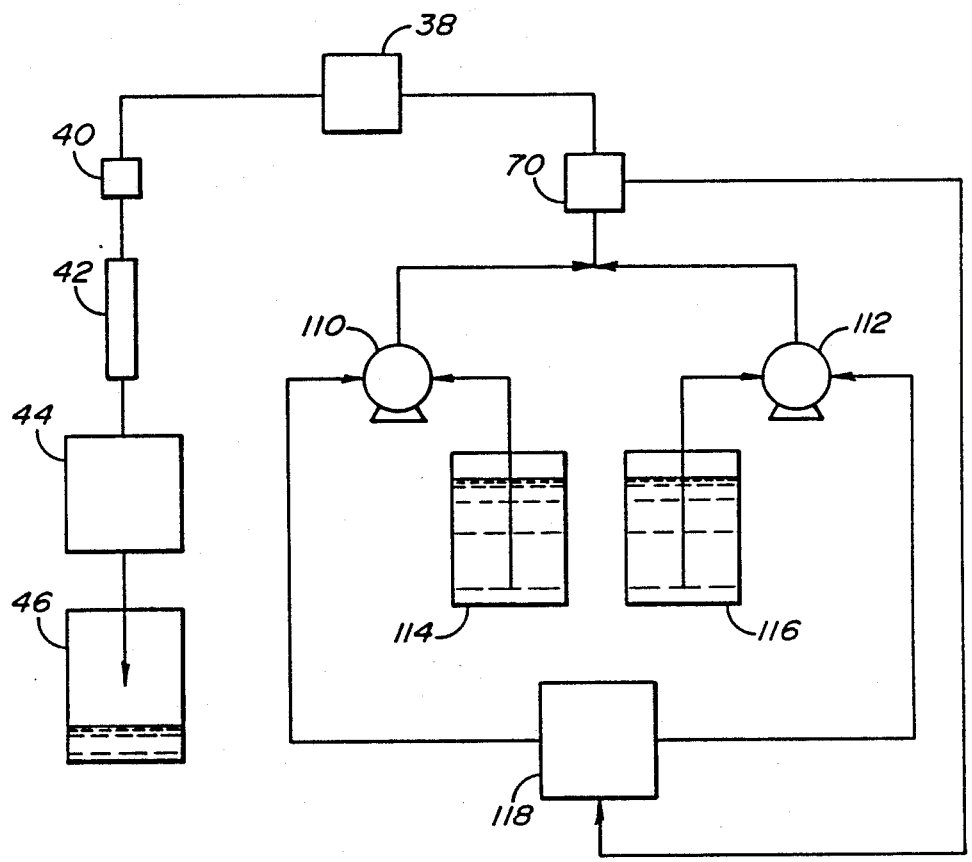
FIG. 10 is a schematic illustration of a dual pump high performance liquid chromotography system including a fluid or solvent delivery system constructed in accordance with the teachings of this invention.

Referring now to FIG. 10, two pumps 110 and 112 are connected in parallel to deliver two different fluids 114, 116 to a liquid chromatographic system 38, 40, 42, 44, 46. Control circuit 118 may control the pumps individually or may control one pump to compensate for the deficit flow of the other.

As is apparent the term "refill period" or the "refill portion of the stroke" as used herein includes the decompression period and not just the period when the inlet check valve is open and the pump chamber is being refilled. Also, the portion of the compression stroke prior to outlet check valve opening has been termed "piston chamber pump-up" or "chamber pump-up" although certain of the prior art include this period within the term "refill". As is obvious when the outlet check valve is closed the pump is "isolated" from the remainder of the fluid system and this period of no flow has been termed the deficit flow period. Still further, the time during which the pump is delivering an excess quantity of fluid to the system has been termed the compensation period or portion of the stroke in certain of the claims. This term is synonymous with the term system pump-up.

As used in the appended claims the term "predetermined" when used in conjunction with flow, speed or velocity is not intended to mean constant and includes a known variable or programmed change. Moreover, unless expressly stated otherwise in the appended claims it is obvious that the speed of the drive motor during the refill, chamber pump-up and compensation periods, need not be either constant or the same and the term "predetermined" is intended to incompass such operation. For example, because of stepper motor torque considerations, it may be desirable to reduce motor speed below the refill speed but above the normal delivery speed and that speed change may come either prior to or during chamber pump-up, at the opening of the outlet check valve, or at some point in the compensation period, i.e. either before, at or after outlet check valve opening.

While there has been discussed in the specification only check valves, the term "valve" in the appended claims is not intended to be so limited. From a commercial standpoint, while check valves may be the valve of choice because of cost, simplicity, ease of repair or replacement, one could utilize other types of valves, such as slider valves, and construct circuitry and sensing systems to open and close the valves at the proper points in the pump cycle.

It should also be understood that although herein the period of excess flow has been described as coming immediately after the piston chamber pump-up period it can come at any time during the delivery cycle. In fact, depending upon the characteristics of the pulse damper, it may be advantageous to have the excess flow period occur just prior to the start of refill. It is also possible to construct a dual or multiple pump system and construct the control circuitry and algorithm such that the pumps are not in refill at the same time and that the delivery speed of one pump is increased during the refill and pump-up cycle of another such that the excess quantity of flow delivered by one pump makes up for the flow deficiency of another. In this manner, almost pulseless flow can be achieved.

There has been illustrated and described a high pressure pump control system suitable for high performance liquid chromatography and in which the pump has a rapid refill and piston chamber pump-up cycle and a rapid system pump-up cycle and in which the control scheme is based upon a determination of the deficit flow period, i.e., that period when the outlet check valve is closed and maintaining the pump at a delivery rate greater than normal delivery rate for a sufficient period of time to make up the deficiency in total flow rate. This allows construction of a solvent delivery system having higher accuracy and reproducibility and less cross-talk when used in multi-pump systems than those of the prior art.

What is claimed is:

1. A fluid delivery apparatus for delivering fluid to a fluid receiving system comprising:
   (a) at least one pump having a piston for reciprocation within a pump chamber, said pump having a fluid inlet and a fluid outlet;
   (b) isolating means for periodically isolating the outlet of said pump from the remainder of the fluid system for a period of time thereby creating a deficit flow period;
   (c) refill means for refilling said pump chamber during said deficit flow period;
   (d) variable piston drive means for driving said piston at various velocities;
   (e) control means connected to said drive means for controlling the speed of said drive means;
   (f) said control means including means for driving said drive means at a first predetermined speed during a normal delivery period to deliver fluid to said system at a normal delivery rate;
   (g) deficit flow determining means for determining the quantity of fluid which would have been delivered during said deficit flow period had said pump been delivering fluid to said system at said normal delivery rate;
   (h) said control means further including compensation means for driving said drive means at a second predetermined speed during a compensation period for a time sufficient to compensate for the deficiency in flow during said deficit flow period.

2. The fluid delivery apparatus of claim 1 wherein said compensation period occurs immediately after said deficit flow period and before said normal delivery period.

3. The fluid delivery apparatus according to claim 2 wherein said control means further includes means for driving said drive means at a third predetermined speed greater than said first predetermined speed during at least a portion of said deficit flow period.

4. The fluid delivery apparatus according to claim 3 wherein said control means drives said drive means at said third predetermined speed during all of said deficit flow period.

5. The fluid delivery apparatus according to claim 1 wherein said first and second predetermined speeds are constant.

6. The fluid delivery apparatus according to claim 3 wherein said first, second and third predetermined speeds are constant.

7. The fluid delivery apparatus according to claim 6 wherein said second and third predetermined speeds are equal.

8. A fluid delivery apparatus according to claim 1 for delivering at least two fluids at predetermined flow rates to said fluid system comprising:
 (a) a plurality of pumps each having its own isolating means, refill means, drive means and deficit flow period;
 (b) said deficit flow determining means determining the deficit flow quantity for each of said pumps; and
 (c) said compensation means including means for compensating each pump for its respective deficit flow.

9. The fluid delivery apparatus according to claim 8 wherein said control means further includes means for driving each of said drive means at a third predetermined speed greater than said first predetermined speed during at least a portion of each respective deficit flow period.

10. The fluid delivery apparatus according to claim 9 wherein said compensation period occurs immediately after said deficit flow period and before said normal delivery period.

11. The method of operating pumping apparatus for delivering fluid to a system, said apparatus including a pump having at least one piston, said pump having (i) a delivery period during which the piston is driven at a first predetermined delivery rate to provide a normal delivery fluid flow rate to said system, (ii) a refill and piston chamber pump-up period during which the output of said pump is isolated from said system creating a deficit flow period during which no fluid is being delivered to said system, the improvement comprising the steps of;
 (a) computing the quantity of fluid that would have been delivered to said system during the deficit flow period had said pump been delivering fluid to said system at its normal delivery rate;
 (b) driving said pump at a speed such that fluid is delivered to said system at a higher rate than said normal delivery rate for a period of time sufficient to compensate for the quantity not delivered during said deficit flow period.

12. The method according to claim 11 wherein the improvement comprises the steps of:
 (a) selecting said higher rate of speed and period of time such that the delivered fluid overcompensates for the flow deficiency.

13. The method according to claim 11 wherein the improvement comprises the steps of:
 (a) selecting said higher rate of speed and period of time such that the delivered fluid undercompensates for the flow deficiency.

14. In a fluid delivery system having a single piston pump and inlet and outlet valves to allow fluid to be drawn into the pump piston chamber during a refill cycle and fluid to be delivered to the outlet of the system at a predetermined flow rate during a normal delivery period and a control means for controlling the pump piston speed, the method of compensating said fluid delivery system for the deficiency in fluid flow during the period when the outlet valve is closed and no fluid is being pumped to said system comprising the steps of:
 (a) determining a first time period approximating the time period when said outlet valve is closed and said fluid delivery system is not delivering fluid at its outlet;
 (b) driving said pump piston at a delivery rate greater than its predetermined normal delivery rate for a second time period such that the excess flow during said second time period approximates the flow deficiency during said first time period.

15. The fluid delivery system of claim 14 wherein:
 (a) the predetermined flow rate during the normal delivery period is constant; and
 (b) the piston speed during at least a portion of said first time period is greater than the piston speed during the normal delivery period to minimize said first time period.

16. The fluid delivery system of claim 15 wherein the pump piston speed during said second time period is approximately equal to the speed during said first time period.

17. The fluid delivery system of claim 14 wherein said second time period and said greater speed are selected such that the excess quantity of fluid delivered to the system exceeds the deficit quantity.

18. The fluid delivery system of claim 14 where said second time period and said greater speed are selected such that the excess quantity of fluid delivered to said system is less than the deficit quantity.

19. Fluid delivery apparatus for delivering fluid to a system comprising:
 (a) a pump having at least one piston for reciprocation within a pump chamber;
 (b) an inlet valve for admitting fluid to said chamber during the refill portion of the stroke of said piston;
 (c) an outlet valve for closing the outlet of said pump during the refill and chamber pump-up portion of the piston stroke, said outlet valve opening to allow discharge of fluid to the system during at least a portion of the pumping stroke;
 (d) variable piston drive means for driving said piston at various speeds;
 (e) control means connected to said drive means for controlling the speed of said drive means;
 (f) said control means including means for driving said drive means at a first predetermined speed during a normal delivery period to deliver to the system a predetermined quantity of fluid per unit of time during such period;
 (g) means for determining the approximate time period during which said outlet valve is closed and said pump is not delivering fluid to the system;
 (h) said control means further including means for driving said drive means at a second predetermined speed greater than said first predetermined speed for a period of time such that the excess fluid flow during said period approximately equals the fluid flow deficiency during the period when said outlet valve is closed.

20. The system according to claim 19 wherein said first predetermined speed is constant such that the fluid flow rate during the normal delivery period is a constant.

21. The system of claim 20 wherein said control means further includes means for driving said drive means at a third predetermined speed greater than said first predetermined speed during the period of time when said outlet valve is closed.

22. The system of claim 21 wherein said second and third predetermined speeds are constant.

23. The system of claim 21 wherein said second and third predetermined speeds are equal.

24. The system according to claim 19 wherein the period of time during which said drive means is being driven at said second predetermined speed commences at approximately the time when the outlet valve opens.

25. The fluid delivery system of claim 19 wherein the excess quantity of fluid delivered exceeds the fluid deficiency.

26. The fluid delivery system of claim 19 wherein the excess quantity of fluid delivered is less than the fluid deficiency.

27. In a fluid delivery system having a pump including at least a single piston for reciprocation within a pump chamber, inlet and outlet check valves, a variable speed pump piston drive means and a control means for controlling the speed of said drive means, said control means (i) driving said drive means at a first predetermined speed during a normal delivery time period for delivering fluid at a first predetermined rate, (ii) driving said drive means at a second predetermined speed during a second time period when the outlet check valve is closed and said pump is in the refill and pump piston chamber pump-up portions of its stroke, the improvement comprising:
    means for determining the length of said second time period;
    said control means including means for driving said drive means at a third predetermined speed greater than said first predetermined speed such that fluid is delivered at a rate larger than said first predetermined rate; and
    means for determining the length of a third time period during which said drive means is operating at said third predetermined speed such that an excess quantity of fluid is delivered during said third time period which approximates the quantity undelivered during said second time period.

28. The fluid delivery system according to claim 27 wherein said means for determining the length of said second time period includes;
    means generating a first signal when said piston begins its refill stroke and said outlet check valve closes;
    means generating a second signal approximating the time when said outlet check valve opens; and
    means for determining the time between said first and second signals.

29. The fluid delivery system according to claim 28 wherein said second signal generating means includes means for directly detecting the opening of said outlet check valve.

30. The fluid delivery system of claim 28 wherein said second signal generating means includes means for inferentially determining the time of opening of said outlet check valve.

31. The fluid delivery system according to claim 27 wherein said means for determining the length of said second time period includes:
    means for determining and storing system pressure during said first time period;
    means operative during said second time period for sampling and holding the time and pressure when piston chamber pressure reaches two predetermined values of pressure less than the stored system pressure;
    means for determining the slope of the piston pressure pump-up waveform;
    means utilizing said determined slope of said piston pressure pump-up waveform for determining the time when said piston chamber pressure would reach a value proportional to said stored system pressure if the outlet check valve remained closed; and
    calculating means utilizing said determined second time period to determine the length of said third time period.

32. The fluid delivery system according to claim 31 wherein said proportional value is less than said sampled system pressure.

33. The fluid delivery system according to claim 31 wherein said proportional value is greater than said sampled system pressure.

34. The fluid delivery system according to claim 31 wherein said proportional value is approximately equal to said sampled system pressure.

35. The method of operating fluid delivery apparatus for delivering fluid to a fluid receiving system, said apparatus including a pump having at least one piston, said pump having (i) a normal delivery period during which said piston is driven at a first predetermined delivery speed to provide a normal delivery fluid flow rate to said system, (ii) a refill and piston chamber pump-up period during which the output of said pump is isolated from said system creating a deficit flow period during which no fluid is being delivered to said system, the improvement comprising the steps of:
    (a) determining the duration of a time period $T_{DF}$ during which the output of said pump is isolated from said system and no fluid is being delivered by said pump to said system;
    (b) solving the equation $$T_{EX} = \frac{F_D}{F_{EX}} \cdot T_{DF}$$

where $F_D$ is the fluid flow rate out of said pump into said system during the normal delivery period and $F_{EX}$ is a fluid flow rate in excess of $F_D$ which will be delivered by the pump to said system during a period of excess flow;
    driving said pump for a period of time equal to $T_{EX}$ at a delivery flow rate of $F_D + F_{EX}$ whereby the quantity of fluid delivered during said time period $T_{EX}$ in excess of the quantity normally delivered during the time period $T_{EX}$ is equal to the quantity of fluid that would have been delivered to said system during the deficit flow period had said pump been delivering fluid to said system at its normal delivery rate.

36. The method according to claim 35 wherein the improvement comprises the steps of:

(a) determining the duration of said time period $T_{DF}$ in such a manner that the determined time period is longer than the actual time period whereby the delivered fluid overcompensates for the flow deficiency.

37. The method according to claim 35 wherein the improvement comprises the steps of:
(a) determining the duration of said time period $T_{DF}$ in such a manner that the determined time period is less than the actual time period whereby the delivered fluid undercompensates for the flow deficiency.

38. A fluid delivery apparatus for delivering fluid to a fluid receiving system comprising:
(a) at least one pump having a piston for reciprocation within a pump chamber, said pump having a fluid inlet and a fluid outlet;
(b) isolating means for periodically isolating the outlet of said pump from the remainder of the fluid system for a period of time $T_{DF}$ thereby creating a deficit flow period;
(c) refill means for refilling said pump chamber during said deficit flow period;
(d) variable piston drive means for driving said piston at various speeds;
(e) control means connected to said drive means for controlling the speed of said drive means;
(f) said control means including means for driving said drive means at a first predetermined speed during a normal delivery period to deliver fluid to said system at a normal delivery rate $F_D$ and at a second predetermined speed greater than said first predetermined speed to delivery fluid to said system at a delivery rate which exceeds the normal delivery rate by an excess delivery rate $F_{EX}$;
(g) means for determining the length of the deficit flow time period $T_{DF}$;
(h) means for solving the equation $$T_{EX} = \frac{F_D}{F_{EX}} \cdot T_{DF}$$

(i) said control means further including means for driving said drive means at said second predetermined speed for approximately said time period $T_{EX}$ whereby the excess quantity of fluid delivered during said time period $T_{EX}$ approximately equals the quantity of fluid which would have been delivered during the time period $T_{DF}$ had said apparatus been delivering fluid during such period at said normal delivery rate.

39. The fluid delivery apparatus of claim 38 wherein said time period $T_{EX}$ occurs immediately after said deficit flow period and before said normal delivery period.

40. The fluid delivery apparatus according to claim 38 wherein said control means further includes means for driving said drive means at a third predetermined speed greater than said first predetermined speed during at least a portion of said deficit flow period.

41. The fluid delivery apparatus according to claim 40 wherein said control means drives said drive means at said third predetermined speed during all of said deficit flow period.

42. The fluid delivery apparatus according to claim 40 wherein said first and second predetermined speeds are constant.

43. The fluid delivery apparatus according to claim 40 wherein said first, second and third predetermined speeds are constant.

44. The fluid delivery apparatus according to claim 43 wherein said second and third predetermined speeds are equal.

45. The fluid delivery apparatus according to claim 38 wherein $T_{DF}$ is determined in such a manner that it exceeds the actual time period such that said apparatus overcompensates for the deficit flow.

46. The fluid delivery apparatus according to claim 38 wherein $T_{DF}$ is determined in such a manner that it is less than the actual time period such that said apparatus undercompensates for the deficit flow.

47. A fluid delivery apparatus according to claim 38 for delivering at least two fluids at predetermined flow rates to said fluid system comprising:
(a) a plurality of pumps each having its own isolating means, refill means, drive means and deficit flow period;
(b) said deficit flow determining means determining independently the deficit flow period for each of said pumps;
(c) said equation solving means solving said equation independently for each of said pumps;
(d) said control means including means for driving each of said pumps at its respective second predetermined speed for its respective calculated time period $T_{EX}$ 48. The fluid delivery apparatus according to claim 47 wherein said control means further includes means for driving each of said drive means at a third predetermined speed greater than said first predetermined speed during at least a portion of each respective deficit flow period.

49. The fluid delivery apparatus according to claim 47 wherein said time period $T_{EX}$ occurs immediately after said deficit flow period and before said normal delivery period.

50. In a fluid delivery apparatus for delivering fluid to a fluid receiving system, said apparatus having at least one single piston pump, inlet and outlet valves to allow fluid to be drawn into the pump piston chamber during a refill cycle and to be delivered under pressure to the system at a predetermined flow rate during a delivery period and control means for controlling the pump piston speed, the method of compensating said fluid delivery apparatus for the quantity of fluid undelivered to said system during the period $T_{DF}$ when the outlet valve is closed, comprising the steps of:
(a) sampling system pressure during the delivery period;
(b) generating a signal approximating the time when the outlet valve closes and the deficit flow time period $T_{DF}$ begins;
(c) sampling and storing pump piston chamber pressure at least two points during the piston delivery stroke when both the inlet and outlet valves are closed;
(d) determining the slope of the piston chamber pressure pump-up waveform;
(e) determining a time when the piston chamber pressure would approximate a percentage of said stored system pressure if the outlet valve remained closed and using said determined time as the end of the deficit flow time period $T_{DF}$;
(f) determining the time period $T_{DF}$;
(g) solving the equation $$T_{EX} = \frac{F_D}{F_{EX}} \cdot T_{DF}$$

where $F_D$ is said predetermined fluid flow rate and $F_{EX}$ is a fluid flow rate in excess of said predetermined flow rate;

(h) driving said pump at a speed sufficient to deliver fluid at a flow rate equal to $F_D+F_{EX}$ for a time equal to $T_{EX}$.

51. The method according to claim 50 wherein said percentage is 90% to 110% of the stored system pressure whereby under or overcompensation occurs.

52. The method according to claim 50 wherein said percentage equals 100% of said stored system pressure.

53. A fluid delivery apparatus for delivering fluid to a fluid receiving system comprising:
 (a) at least one pump having a piston for reciprocation within a pump chamber, said pump having a fluid inlet and a fluid outlet;
 (b) isolating means for periodically isolating the outlet of said pump from the remainder of the fluid system for a first time period thereby creating a deficit flow period;
 (c) refill means for refilling said pump chamber during said deficit flow period;
 (d) variable piston drive means for driving said piston at various velocities;
 (e) control means connected to said drive means for controlling the speed of said drive means;
 (f) said control means including means for driving said drive means at a first predetermined speed during a normal delivery period to deliver fluid to said system at a normal delivery rate;
 (g) said control means including means for driving said pump at a second predetermined speed greater than said first predetermined speed for a second time period such that the excess quantity of fluid delivered during said second time period approximates the quantity of fluid which would have been delivered during said first time period had said pump been delivering fluid at said normal delivery rate during said first time period.

54. A fluid delivery apparatus for delivering fluid to a fluid receiving system comprising:
 (a) at least one pump having a piston for reciprocation within a pump chamber, said pump having a fluid inlet and a fluid outlet;
 (b) isolating means for periodically isolating the outlet of said pump from the remainder of the fluid system for a period of time $T_{DF}$ thereby creating a deficit flow period;
 (c) refill means for refilling said pump chamber during said deficit flow period;
 (d) variable piston drive means for driving said piston at various speeds;
 (e) control means connected to said drive means for controlling the speed of said drive means;
 (f) said control means including means for driving said drive means at a first predetermined speed during a normal delivery period to deliver fluid to said system at a normal delivery rate $F_D$ and at a second predetermined speed greater than said first predetermined speed to delivery fluid to said system at a delivery rate which exceeds the normal delivery rate by an excess delivery rate $F_{EX}$;
 (g) means for determining the length of the deficit flow time period $T_{DF}$;
 (h) means for solving the equation $$\int_0^{T_{EX}} F_{EX}\,dt = \int_0^{T_{DF}} F_D\,dt$$

for the quantity $T_{EX}$
 (i) said control means further including means for driving said drive means at said second predetermined speed for approximately said time period $T_{EX}$ whereby the excess quantity of fluid delivered during said time period $T_{EX}$ approximately equals the quantity of fluid which would have been delivered during the time period $T_{DF}$ had said apparatus been delivering fluid during such period at said normal delivery rate.

55. A fluid delivery system comprising:
 (a) a plurality of pumps each including at least one piston for reciprocation within a pumping chamber, an outlet valve for periodically isolating the outlet of said pump from the remainder of the fluid system for a time period $T_{DF}$ thereby creating a deficit flow period during which no fluid is delivered by said pump to the remainder of the fluid system;
 (b) variable piston drive means for driving each of said pistons at various speeds;
 (c) control means connected to said drive means for controlling the speed of said drive means;
 (d) refill means for refilling each of said pump-up chambers with fluid during the respective deficit flow period of each said pump;
 (e) means for determining the time period $T_{DF}$ for each of said pumps;
 (f) said control means including means for driving each of said drive means at a first predetermined speed during a normal delivery period to deliver fluid to said system at a normal delivery rate;
 (g) said control means further including compensating means for driving each of said drive means at a second predetermined speed greater than said first delivery speed for a second period of time such that the excess flow during said second period of time approximates the deficit flow during a time period $T_{DF}$.

56. The fluid delivery system according to claim 55 wherein the compensating means of one pump compensates for the deficit flow of another pump.

57. The fluid delivery system according to claim 55 wherein the compensating means of each pump compensates for its own deficit flow.

58. A fluid delivery apparatus according to claim 1 for delivering a plurality of fluids at predetermined flow rates to said fluid receiving system comprising:
 (a) a plurality of pumps each having its own isolating means, refill means, drive means and deficit flow;
 (b) said deficit flow determining means determining the deficit flow quantity for each of said pumps; and
 (c) said compensation means including means for compensating for the deficit flow of at least one of said pumps.

59. The fluid delivery apparatus of claim 58 wherein said compensating means includes means for compensating each pump for its respective deficit flow.

60. The fluid delivery apparatus of claim 58 wherein said compensating means includes means for driving said drive means of at least one of said pumps at said second predetermined speed for a time sufficient to compensate for the deficit flow occurring in at least one of the other of said pumps.

61. The fluid delivery apparatus of claim 58 wherein said compensating means includes means for driving said drive means of each of said pumps at said second predetermined speed for a time sufficient to compensate for the deficit flow occurring in another of said pumps.

* * * * *

UNITED STATES PATENT AND TRADEMARK OFFICE
CERTIFICATE OF CORRECTION

PATENT NO. : 4,919,595
DATED : April 24, 1990
INVENTOR(S) : Robert K. Likuski and Scott N. MacDonald It is certified that error appears in the above-identified patent and that said Letters Patent is hereby corrected as shown below:

Column 6, line 50, equation (3) should appear as follows:

$$Q_{EX} = \int_0^{T_{EX}} F_{EX}\, dt \tag{3}$$

Column 11, lines 15 to 23, equations (7) and (8) should appear as follows:

$$Q_{EX} = \int_0^{T_{EX}} F_{EX}\, dt \tag{7}$$

$$Q_{DF} = \int_0^{T_{DF}} F_D\, dt \tag{8}$$

UNITED STATES PATENT AND TRADEMARK OFFICE
CERTIFICATE OF CORRECTION

PATENT NO. : 4,919,595

DATED : April 24, 1990

INVENTOR(S) : Robert K. Likuski and Scott N. MacDonald

It is certified that error appears in the above-identified patent and that said Letters Patent is hereby corrected as shown below:

Column 22, line 5, the equation should read as follows:

$$\int_0^{T_{EX}} F_{EX} dt = \int_0^{T_{DF}} F_D dt$$

Signed and Sealed this

Eleventh Day of June, 1991

*Attest:*

HARRY F. MANBECK, JR.

*Attesting Officer*  *Commissioner of Patents and Trademarks*